United States Patent [19]
Dooley et al.

[11] Patent Number: 5,367,053
[45] Date of Patent: Nov. 22, 1994

[54] OPIOID PEPTIDE INHIBITORS

[75] Inventors: Colette T. Dooley, San Diego; Richard A. Houghten, Del Mar, both of Calif.

[73] Assignee: Houghten Pharmaceuticals, Inc., San Diego, Calif.

[21] Appl. No.: 64,517

[22] Filed: May 19, 1993

[51] Int. Cl.[5] .................. A61K 37/02; C07K 5/00; C07K 7/00; C07K 15/00
[52] U.S. Cl. .................................... 530/329; 530/328
[58] Field of Search ............................... 530/328, 329

[56] References Cited

U.S. PATENT DOCUMENTS

| | | | |
|---|---|---|---|
| 4,833,092 | 5/1989 | Geysen | 436/501 |
| 5,010,175 | 4/1991 | Rutter et al. | 580/334 |
| 5,194,392 | 3/1993 | Geysen | 436/518 |

OTHER PUBLICATIONS

Houghten et al., "Generation and use of synthetic peptide combinatorial libraries for basic research and drug discovery" *Nature* 354:84–86 (1991).

Houghten et al., "The Use of Synthetic Peptide Combinatorial Libraries for the Identification of Bioactive Peptides" *Biotechniques* 13:412–421 (1992).

Pinilla et al., "Rapid Identification of High Affinity Peptide Ligands Using Positional Scanning Synthetic Peptide Combinatorial Libraries" *Biotechniques* 13:901–905 (1992).

Dooley and Houghten, "The Use of Positional Scanning Synthetic Peptide Combinatorial Libraries for the Rapid Determination of Opioid Receptor Ligands" *Life Sciences* 52:1509–1517 (1993).

Simon et al., "Peptoids: a Modular Approach to Drug Discovery" *PNAS* 89:9367–9371 (1992).

*Primary Examiner*—Robert J. Hill, Jr.
*Assistant Examiner*—Sheela J. Huff
*Attorney, Agent, or Firm*—Campbell and Flores

[57] ABSTRACT

This invention provides novel peptides having the ability to inhibit binding of the mu specific ligand $^3$H-[D-Ala$^2$,MePhe$^4$,Gly-ol$^5$]enkephalin ("DAGO") to the opioid receptors in crude rat brain homogenate.

4 Claims, 4 Drawing Sheets

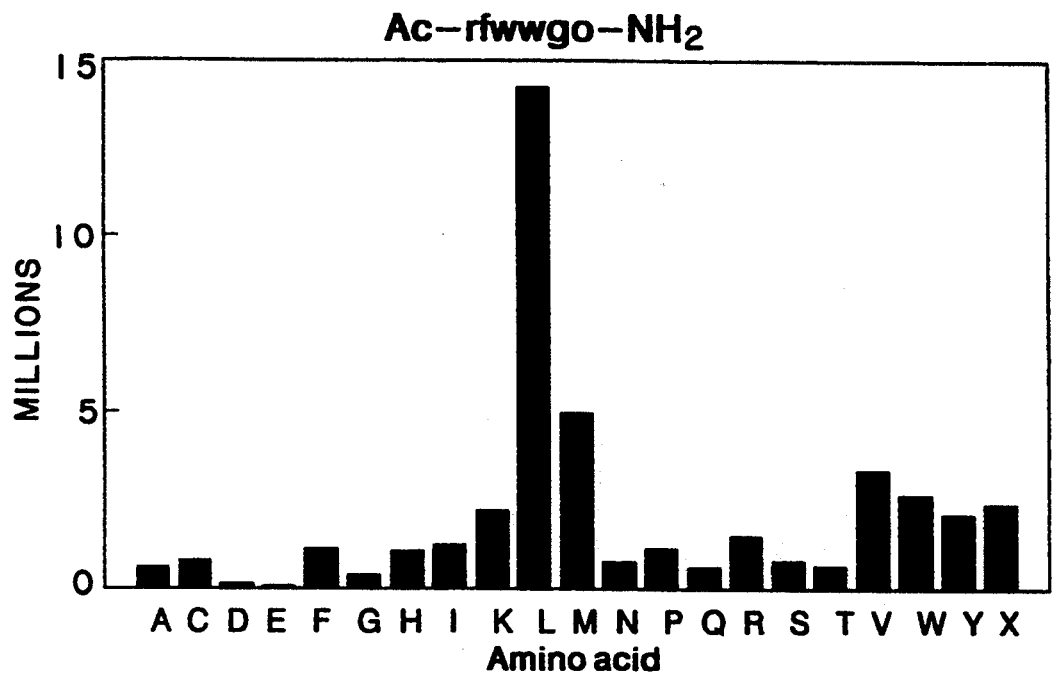
FIG. IA

Ac-rfwmyo-NH₂

| | nM |
|---|---|
| Ac-rfwmyr | 137 |
| Ac-rfwmyk | 279 |
| Ac-rfwmyx | 366 |
| Ac-rfwmyh | 370 |
| Ac-rfwmys | 659 |
| Ac-rfwmyt | 697 |
| Ac-rfwmyq | 707 |
| Ac-rfwmyp | 720 |
| Ac-rfwmya | 816 |
| Ac-rfwmyn | 833 |
| Ac-rfwmyg | 922 |
| Ac-rfwmyy | 1044 |
| Ac-rfwmyl | 1457 |
| Ac-rfwmym | 2281 |
| Ac-rfwmyf | 3730 |
| Ac-rfwmyc | 3769 |
| Ac-rfwmyw | 3800 |
| Ac-rfwmye | 4496 |
| Ac-rfwmyd | 4980 |
| Ac-rfwmyv | 12402 |
| Ac-rfwmyi | 53641 |

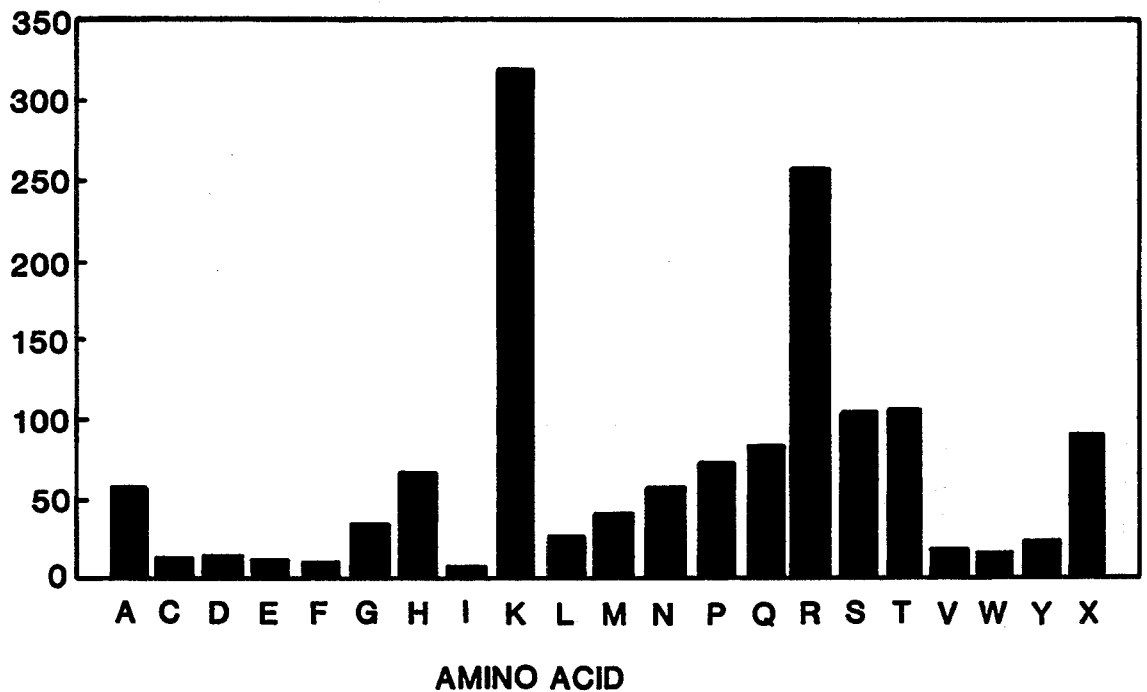
| Ac-RFMWMTO-NH$_2$ | nM |
|---|---|
| Ac-RFMWMTK | 3 |
| Ac-RFMWMTR | 4 |
| Ac-RFMWMTT | 9 |
| Ac-RFMWMTS | 10 |
| Ac-RFMWMT | 11 |
| Ac-RFMWMTQ | 12 |
| Ac-RFMWMTP | 14 |
| Ac-RFMWMTH | 15 |
| Ac-RFMWMTA | 18 |
| Ac-RFMWMTN | 18 |
| Ac-RFMWMTM | 25 |
| Ac-RFMWMTG | 31 |
| Ac-RFMWMTL | 40 |
| Ac-RFMWMTY | 42 |
| Ac-RFMWMTV | 52 |
| Ac-RFMWMTW | 63 |
| Ac-RFMWMTD | 80 |
| Ac-RFMWMTC | 87 |
| Ac-RFMWMTE | 93 |
| Ac-RFMWMTF | 96 |
| Ac-RFMWMTI | 161 |
FIG. IC Ac-rfwino-NH₂

| | nM |
|---|---|
| Ac-rfwink | 16 |
| Ac-rfwina | 33 |
| Ac-rfwinr | 34 |
| Ac-rfwinx | 103 |
| Ac-rfwinq | 120 |
| Ac-rfwinp | 125 |
| Ac-rfwinn | 137 |
| Ac-rfwins | 142 |
| Ac-rfwiny | 155 |
| Ac-rfwinm | 159 |
| Ac-rfwing | 198 |
| Ac-rfwint | 244 |
| Ac-rfwinh | 277 |
| Ac-rfwinw | 826 |
| Ac-rfwinl | 897 |
| Ac-rfwinf | 1002 |
| Ac-rfwine | 1149 |
| Ac-rfwinc | 1311 |
| Ac-rfwinv | 1599 |
| Ac-rfwind | 1909 |
| Ac-rfwini | 8000 |

OPIOID PEPTIDE INHIBITORS

BACKGROUND OF THE DISCLOSURE

This invention generally relates to novel peptides having the ability to inhibit ligand binding to an opioid receptor.

There are at least three known subtypes of opioid receptors, mu, kappa, and delta; with some evidence for two additional receptor subtypes. The use of synthetic peptides has been instrumental in the delineation of these subtypes and for providing analogues that can be used for studying the interactions of ligands specific to these receptor systems in both in vitro and in vivo systems.

Recent advances in methods for the preparation and screening of a large numbers of individual peptides has enabled a large number of peptides to be used in all areas biomedical research, including research regarding the interaction of a ligand to the opiate receptor. Even with these advances, however, basic research and drug discovery has been limited by the availability of the requisite large number of diverse opiate agonists and antagonists required to ascertain the relationship between a ligand for a particular opiate receptor subtype. Thus, a need exists for large numbers of individual peptides for use in biomedical research, including those for the study of opiate ligand-receptor interactions. This invention satisfies this need and provides related advantages as well.

SUMMARY OF THE INVENTION

This invention provides novel peptides having the ability to inhibit $^3$H-[D-Ala$^2$,MePhe$^4$,Gly-ol$^5$]enkephalin ("DAGO") binding to opioid receptors in crude rat brain homogenates. The novel peptides fall within four general structures: Ac-L-Arg-L-Phe-L-Met-L-Trp-L-Met-L-Thr-L-Xaa-NH$_2$ (SEQ ID NO: 1); Ac-D-Arg-D-Phe-D-Trp-D-Trp-D-Gly-D-Xaa-NH$_2$ (SEQ ID NO: 2); Ac-D-Arg-D-Phe-D-Trp-D-Ile-D-Asn-D-Xaa-NH$_2$ (SEQ ID NO: 3); and Ac-D-Arg-D-Phe-D-Trp-D-Met-D-Tyr-D-Xaa-NH$_2$ (SEQ ID NO: 4). Within each genus, Xaa is substituted by a specific amino acid.

BRIEF DESCRIPTION OF THE FIGURES

FIGS. 1A through 1D graphically depict the ability of each peptide to inhibit binding of [$^3$H]-DAGO to the $\mu$ receptor as measured by the radio-receptor assay. In these FIGURES, "o" is the equivalent of the amino acid code "Xaa".

DETAILED DESCRIPTION OF THE INVENTION

Figure 1B:
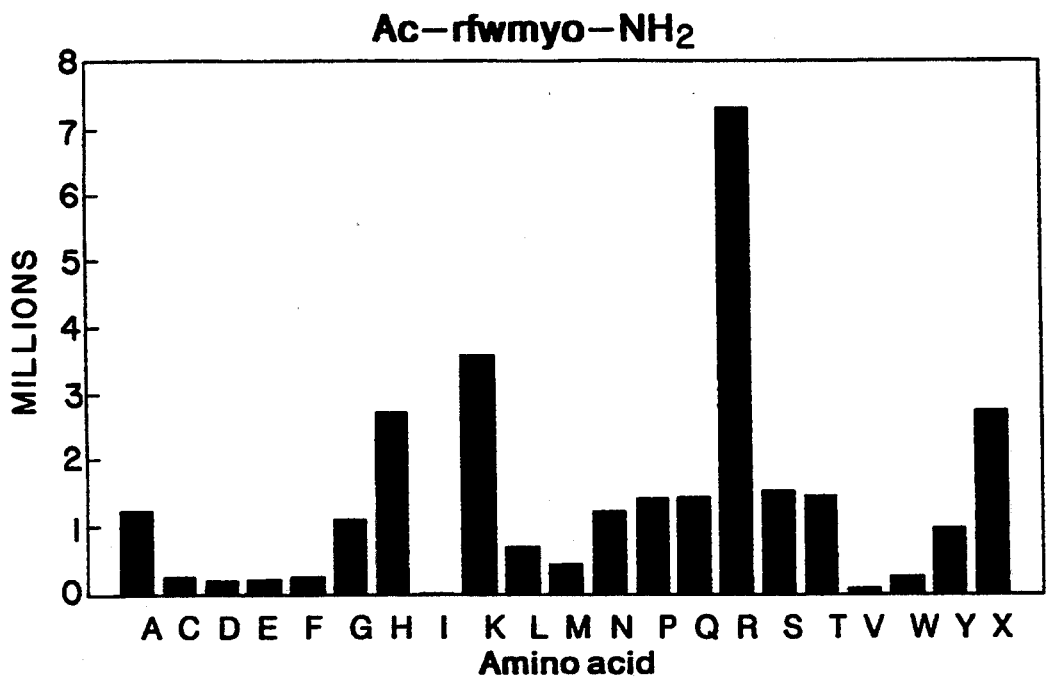

This invention provides peptides useful as inhibitors of $^3$H-[D-Ala$^2$,MePhe$^4$,Gly-ol$^5$]enkephalin ("DAGO") which is known to bind with high selectivity to the $\mu$ ("mu") opioid receptor subtype. Each of the peptides has an acetyl group ("Ac") at the N-terminus and an amide group ("NH$_2$") on the C-terminus. In one embodiment, the peptide has the structure Ac-L-Arg-L-Phe-L-Met-L-Trp-L-Met-L-Thr-L-Xaa-NH$_2$, wherein Xaa is an L-amino acid such as L-Lys, L-Arg, L-Thr, L-Ser, L-Gln, L-Pro, L-His, L-Ala, L-Asn, L-Met, L-Gly, L-Leu, L-Tyr, L-Val, L-Trp, L-Asp, L-Cys, L-Glu, L-Phe, and L-Ile (SEQ ID NO: 1). In another embodiment, the peptide is described by the formula Ac-D-Arg-D-Phe-D-Trp-D-Trp-D-Gly-D-Xaa-NH$_2$, wherein D-Xaa is D-Leu, D-Met, D-Val, D-Trp, D-Lys, D-Tyr, D-Arg, D-Ile, D-Pro, D-Phe, D-His, D-Ser, D-Cys, D-Asn, D-Thr, D-Gln, D-Ala, D-Gly, D-Asp, or D-Glu (SEQ ID NO: 2). Also within the scope of this invention is a peptide having the structure Ac-D-Arg-D-Phe-D-Trp-D-Ile-D-Asn-D-Xaa-NH$_2$, wherein D-Xaa is a D-amino acid such as D-Lys, D-Ala, D-Arg, D-Gln, D-Pro, D-Asn, D-Ser, D-Tyr, D-Met, D-Gly, D-Thr, D-His, D-Trp, D-Leu, D-Phe, D-Glu, D-Cys, D-Val, D-Asp and D-Ile (SEQ ID NO: 3). Further provided by this invention is a peptide having the structure Ac-D-Arg-D-Phe-D-Trp-D-Met-D-Tyr-D-Xaa-NH$_2$, wherein D-Xaa is a D-amino acid such as D-Arg, D-Lys, D-His, D-Ser, D-Thr, D-Gln, D-Pro, D-Ala, D-Ash, D-Gly, D-Tyr, D-Leu, D-Met, D-Phe, D-Cys, D-Trp, D-Glu, D-Asp, D-Val, or D-Ile (SEQ ID NO: 4).

One skilled in the art, using the above formulae, can easily reproduce the peptides of this invention by synthesis on an automated peptide synthesizer (Model 430A, Applied Biosystem, Foster City, Calif. USA) utilizing the directions provided by the manufacturer. After manufacture, the peptides are assayed for receptor binding activity using the radio-receptor assay outlined below. Because these peptides bind to the $\mu$ and other receptor subtypes, they can be used in in vitro assays to study the opiate receptor subtypes. For example, in a sample receptor of unknown type or origin, the peptides, after being labeled with a detectable marker such as a radioisotope, can be contacted with the receptor sample under conditions which specifically favor a particular receptor subtype binding to the peptide(s). Unbound receptor and peptide can be removed, for example, by washing with a saline solution, and bound receptor can then be detected using methods well known to those skilled in the art.

In addition to the peptides utility in in vitro screening method for assaying organic compounds having specificity for the opioid receptors, the peptides also are useful as drugs to treat pathologies associated with other compounds which interact with the opioid receptor system. It can be envisioned that these peptides can be used for therapeutic purposes to block the peripheral effects of existing centrally acting pain killers such as morphine. Since it is known that the majority of peptides do not readily cross the blood-brain barrier (and therefore elicit no central effect), and since morphine has a number of deleterious effects in the periphery which are not required for the desired analgesic effects, it can be anticipated that the subject peptides may have value in blocking the constipation and pruritis (itching) associated with morphine. The novel peptides claimed can be incorporated into pharmaceutical compositions. The pharmaceutical composition is prepared by combining the peptide with a pharmaceutically acceptable carrier. As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents.

Methods of administering a pharmaceutical are well known in the art and include but are not limited to administration orally, intravenously, intramuscularly or intraperitoneal. Administration can be effected continuously or intermittently and will vary with the subject and is dependent on the type of treatment and potency of the peptide used.

Radio-Receptor Assay

Crude membrane homogenates were prepared using a modification of the method described by Paternak, G. W. et al., *Mol. Pharmacol.*, 11:340–351 (1975), incorporated herein by reference. Rat brains frozen in liquid nitrogen were obtained from Rockland, Inc. (Gilberstville, Pa.). The brains were thawed the cerebella removed, and the remaining tissue weighed. Each brain was individually homogenized in 40 ml Tris-HCl buffer (50 mM, pH 7.4, 4° C.) and centrifuged (Sorvall RC5C SA-600 16,000 rpm) for 10 minutes. The pellets were resuspended in fresh Tris-HCl buffer and incubated at 37° C. for 40 minutes. Following incubation, the suspensions were centrifuged as before, the resulting pellets resuspended in 100 volumes of Tris buffer, and the suspensions combined. Membrane suspensions were prepared and used in the same day. Protein content of the crude homogenates ranged from 0.15 to 0.2 mg/ml as determined using the method described by Bradford, M. M. *Anal. Biochem.* 72:248–254 (1976), incorporated herein by reference.

Figure 1D:
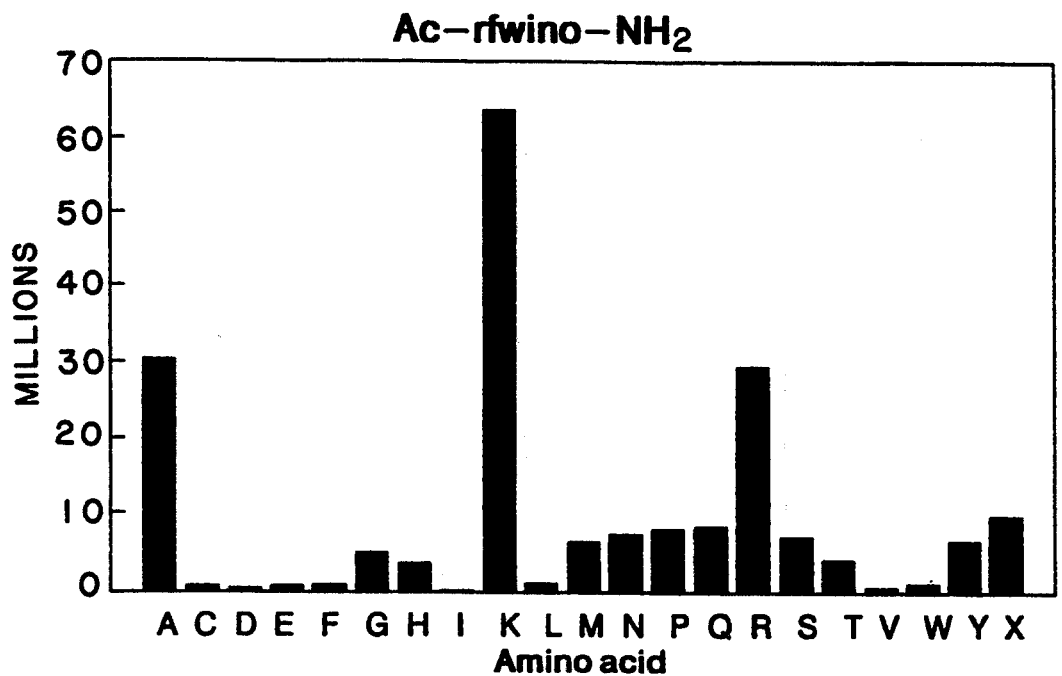

Binding assays were carried out in polypropylene tubes. Each tube contained 0.5 ml of membrane suspension, 8nM[$^3$H]-DAGO (specific activity 36Ci/mmole, 160,000 cpm), 0 0.08 mg/ml peptide mixture and Tris-HCl buffer in a total volume of 0.65 ml. Assay tubes were incubated for 60 minutes at 25° C. The reaction was terminated by filtration through GF-B filters. The filters were subsequently washed with 6 ml Tris-HCl buffer, at 4° C. Bound radioactivity was counted on an LKB Beta-plate Liquid Scintillation Counter and expressed in counts per minute (cpm). Inter- and intra-assay variation standard curves were determined by incubation of [$^3$H]-DAGO in the presence of a range of concentrations of unlabeled DAGO (0.13–3900 nM). Both the tritiated and non-tritiated forms of DAGO were obtained from the National Institute of Drug Abuse (NIDA) repository, as prepared by Multiple Peptide Systems (San Diego, Calif.). A control curve was included on each plate for each assay (using a 96-well format). Competitive inhibition assays were performed as above using serial dilutions of the peptide mixture. IC$_{50}$ values (the concentration necessary to inhibit 50% of [$^3$H]-DAGO binding) were then calculated using the software GRAPHPAD (ISI, San Diego, Calif.) and were found to be consistent in three determinations. The average values for each peptide are presented in FIG. 1.

Although the invention has been described with reference to the disclosed embodiments, it should be understood that various modifications can be made without departing from the spirit of the invention. Accordingly, the invention is limited only by the following claims.

What is claimed is:

1. A peptide having the structure:
   Ac-L-Arg-L-Phe-L-Met-L-Trp-L-Met-L-Thr-L-Xaa-NH$_2$;
   wherein L-Xaa is an L-amino acid selected from the group consisting of L-Lys, L-Arg, L-Thr, L-Ser, L-Gln, L-Pro, L-His, L-Ala, L-Asn, L-Met, L-Gly, L-Leu, L-Tyr, L-Val, L-Trp, L-Asp, L-Cys, L-Glu, L-Phe, and L-Ile (SEQ ID NO: 1).

2. A peptide having the structure:
   Ac-D-Arg-D-Phe-D-Trp-D-Trp-D-Gly-D-Xaa-NH$_2$;
   wherein D-Xaa is a D-amino acid selected from the group consisting of D-Leu, D-Met, D-Val, D-Trp, D-Lys, D-Tyr, D-Arg, D-Ile, D-Pro, D-Phe, D-His, D-Ser, D-Cys, D-Asn, D-Thr, D-Gln, D-Ala, D-Gly, D-Asp, and D-Glu (SEQ ID NO: 2).

3. A peptide having the structure:
   Ac-D-Arg-D-Phe-D-Trp-D-Ile-D-Asn-D-Xaa-NH$_2$;
   wherein D-Xaa is a D-amino acid selected from the group consisting of D-Lys, D-Ala, D-Arg, D-Gln, D-Pro, D-Asn, D-Ser, D-Tyr, D-Met, D-Gly, D-Thr, D-His, D-Trp, D-Leu, D-Phe, D-Glu, D-Cys, D-Val, D-Asp and D-Ile (SEQ ID NO: 3).

4. A peptide having the structure:
   Ac-D-Arg-D-Phe-D-Trp-D-Met-D-Tyr-D-Xaa-NH$_2$;
   wherein D-Xaa is a D-amino acid selected from the group consisting of D-Arg, D-Lys, D-His, D-Ser, D-Thr, D-Gln, D-Pro, D-Ala, D-Asn, D-Gly, D-Tyr, D-Leu, D-Met, D-Phe, D-Cys, D-Trp, D-Glu, D-Asp, D-Val, and D-Ile (SEQ ID NO: 4).

---

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( i x ) FEATURE:
        ( A ) NAME/KEY: Peptide
        ( B ) LOCATION: 7
        ( D ) OTHER INFORMATION: /note=
            " Peptides contain all L-amino acids.
            Xaa=an L- amino acid and can be Lys,
            Arg, Thr, Ser, Gln, Pro, His, Ala,
            Asn, Met, Gly, Leu, Tyr, Val, Trp,
            Asp, Cys, Glu, Phe and Ile."

( x i ) SEQUENCE DESCRIPTION: SEQ ID NO:1:

```
        Arg Phe Met Trp Met Thr Xaa
        1                   5
```

( 2 ) INFORMATION FOR SEQ ID NO:2:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( i x ) FEATURE:
        ( A ) NAME/KEY: Peptide
        ( B ) LOCATION: 6
        ( D ) OTHER INFORMATION: /note=
            " Peptides contain all D-amino acids.
            Xaa=a D- amino acid and can be Leu,
            Met, Val, Trp, Lys, Tyr, Arg, Ile,
            Pro, Phe, His, Ser, Cys, Asn, Thr,
            Gln, Ala, Gly, Asp and Glu."

( x i ) SEQUENCE DESCRIPTION: SEQ ID NO:2:

```
        Arg Phe Trp Trp Gly Xaa
        1                   5
```

( 2 ) INFORMATION FOR SEQ ID NO:3:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( i x ) FEATURE:
        ( A ) NAME/KEY: Peptide
        ( B ) LOCATION: 6
        ( D ) OTHER INFORMATION: /note=
            " Peptides contain all D-amino acids.
            Xaa=a D- amino acid and can be Lys,
            Ala, Arg, Gln, Pro, Asn, Ser, Tyr,
            Met, Gly, Thr, His, Trp, Leu, Phe,
            Glu, Cys, Val, Asp and Ile."

( x i ) SEQUENCE DESCRIPTION: SEQ ID NO:3:

```
        Arg Phe Trp Ile Asn Xaa
        1                   5
```

( 2 ) INFORMATION FOR SEQ ID NO:4:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( i x ) FEATURE:
        ( A ) NAME/KEY: Peptide
        ( B ) LOCATION: 6
        ( D ) OTHER INFORMATION: /note=
            " Peptides contain all D-amino acids.
            Xaa=a D- amino acid and can be Arg,
            Lys, His, Ser, Thr, Gln, Pro, Ala,
            Asn, Gly, Tyr, Leu, Met, Phe, Cys,
            Trp, Glu, Asp, Val and Ile."

( x i ) SEQUENCE DESCRIPTION: SEQ ID NO:4:

```
        Arg Phe Trp Met Tyr Xaa
        1                   5
```

* * * * *

UNITED STATES PATENT AND TRADEMARK OFFICE
CERTIFICATE OF CORRECTION

PATENT NO. : 5,367,053
DATED : November 22, 1994
INVENTOR(S) : Dooley and Houghten It is certified that error appears in the above-indentified patent and that said Letters Patent is hereby corrected as shown below:

On the title page, item [54] and col. 1.
In the title please insert --Novel-- before the word "Opioid".

Column 2, line 14, please delete "D-Ash" and substitute therefor --D-Asn--.

Column 3, line 26, please delete "0 0.08" and substitute therefor --0.08--.

Column 4, line 32, please delete "D-Gin" and substitute therefor --D-Gln--.

Signed and Sealed this

Twenty-eight Day of March, 1995

Attest:

BRUCE LEHMAN

Attesting Officer

Commissioner of Patents and Trademarks